United States Patent [19]

Jones

[11] Patent Number: 5,202,637

[45] Date of Patent: Apr. 13, 1993

[54] FAULT DETECTION IN ELECTROCHEMICAL GAS SENSING EQUIPMENT

[75] Inventor: Gareth J. Jones, Great Abington, United Kingdom

[73] Assignee: Neotronics Limited, Hertfordshire, United Kingdom

[21] Appl. No.: 761,976

[22] PCT Filed: Apr. 4, 1990

[86] PCT No.: PCT/GB90/00507

§ 371 Date: Sep. 25, 1991

§ 102(e) Date: Sep. 25, 1991

[87] PCT Pub. No.: WO90/12315

PCT Pub. Date: Oct. 18, 1990

[30] Foreign Application Priority Data

Apr. 4, 1989 [GB] United Kingdom ............... 8907564

[51] Int. Cl.5 .................................. G01N 27/00
[52] U.S. Cl. .................................. 324/425; 204/401; 324/71.1
[58] Field of Search ............... 324/425, 71.1, 439; 204/401

[56] References Cited

U.S. PATENT DOCUMENTS

| 3,661,748 | 5/1972 | Blackmer | 204/401 |
|---|---|---|---|
| 3,718,568 | 2/1973 | Neuwelt . | |
| 3,776,832 | 12/1973 | Oswin et al. . | |
| 4,443,763 | 4/1984 | Marsoner . | |
| 4,900,422 | 2/1990 | Bryan et al. | 204/401 |
| 4,956,063 | 9/1990 | Hale | 204/401 |
| 4,985,123 | 1/1991 | Curley | 204/401 |
| 5,016,201 | 5/1991 | Bryan et al. | 204/401 |

FOREIGN PATENT DOCUMENTS

| 0039549 | 11/1981 | European Pat. Off. . | |
|---|---|---|---|
| 0220896 | 5/1987 | European Pat. Off. . | |
| 636447 | 5/1983 | Switzerland . | |
| 1006988 | 3/1983 | U.S.S.R. | 324/71.1 |
| 1101101 | 1/1968 | United Kingdom . | |
| 1385201 | 2/1975 | United Kingdom . | |
| 2065309 | 6/1981 | United Kingdom . | |

Primary Examiner—Jack B. Harvey
Assistant Examiner—Maura K. Regan
Attorney, Agent, or Firm—Kerkam, Stowell, Kondracki & Clarke

[57] ABSTRACT

A circuit is described which tests whether an amperometric electrochemical gas sensor monitoring the concentration of toxic gases in an atmosphere is working properly. The sensor has a sensing electrode, a reference electrode, and a counter electrode and in normal operation the potential between the reference electrodes is fixed by means of an operational amplifier. When there is gas in the atmosphere, the gas reacts electrochemically at the sensing electrode, causing the amplifier to supply electrical current to the counter electrode which results in an electrical potential to the sensor that is proportional to the amount of toxic gas in the atmosphere. The sensor is periodically tested to determine whether it is working properly by applying a pulse potential between the sensing and reference electrodes. If a current flow results then a signal is sent to an alarm device.

11 Claims, 3 Drawing Sheets

FAULT DETECTION IN ELECTROCHEMICAL GAS SENSING EQUIPMENT

TECHNICAL FIELD

The present invention relates to a gas monitor incorporating one or more amperometric gas sensors and in particular it relates to improvements in the electronic circuits of the monitors allowing the monitor to test that the sensor is working properly.

BACKGROUND ART

Gas monitors are known that include one or more replaceable amperometric gas sensors providing an electrical current the magnitude of which provides a measure of the amount of gas detected in an atmosphere. This signal is analysed by circuitry within the monitor to give a monitor output which may be in the form of a display (in an analogue or digital form) of the amount of a specific gas detected and/or the output may be a printer or plotter and/or an alarm to give an audible and/or visual warning if the concentration of a gas falls to an undesirable level or if the concentration of a gas arises above a certain threshold level; the output signal could be recorded for subsequent analysis. However, the gas monitor need not necessarily give a direct indication of the amount of gas detected but may use the signal from one or more sensors to compute another parameter which may be displayed or printed; thus, the signal from a gas sensor may be used, together with other measurements, to compute the efficiency of a boiler (see British Patent No. 2,064,780).

The sensors used in the monitors of the present invention are amperometric electrochemical sensors of the type having a sensing (or working) electrode which is in communication with the atmosphere being sensed, a counter electrode and a reference electrode and all three electrodes are in contact with electrolyte within the sensor and are connected via respective terminals to the circuitry within the monitor; sensors of this type will be eferred to herein as "three electrode sensors". The potential difference between the sensing electrode and the reference electrode may be controlled and in some sensors this is done by connecting these two electrodes to the inputs of an operational amplifier either directly or through a resistor, e.g. see British Patent Specification Nos. 1,101,101 and 1,385,201 and U.S. Pat. No. 3,776,832 and European Patent Application No. 0,220,896A.

A circuit generally in accordance with the above patents is set out in FIG. 1 of the accompanying drawings. In FIG. 1, the sensor is indicated by the general reference number 10 and includes an electrolyte (sulphuric acid), a sensing electrode 12, a reference electrode 14 and a counter electrode 16 all of which are in contact with the electrolyte. The sensing electrode and the reference electrode are joined via terminals 12a and 14a to respective inputs of an operational amplifier 18 whose output is connected to the counter electrode 16 via terminal 16a. A resistor 20 is present between the sensing electrode 12 and its input to the operational amplifier 18. The sensing electrode 12 is in contact with an atmosphere that is being monitored and when the atmosphere contains a gas of the type being detected, this gas undergoes an electrochemical reaction which depolarizes the sensing electrode 12 causing the potential of that electrode to alter and so cause an imbalance between the potential of the sensing electrode 12 and the reference electrode 14 and hence between the inputs of the operational amplifier 18. The potential difference between the operational amplifier inputs causes the operational amplifier to supply current through its output to counter electrode 16 and hence causes a current to flow in the sensor cell 10 between the counter electrode 16 and the sensing electrode 12 (however substantially no current flows between the reference electrode and the sensing electrode). The current flowing through the sensor cell, which is directly related to the amount of gas in the atmosphere, can be measured, for example, by including a resistor between the amplifier output and the counter electrode 16 and measuring the voltage drop across the resistor (see U.S. Pat. No. 3,776,832); alternatively, the current flowing through the cell may be measured by a current follower connected to line 22 or by measuring the potential difference across a resistor between line 22 and a ground or other fixed potential (see European Patent Application No. 0,220,896); alternatively, the voltage drop across the resistor 20 may be measured (see British Patent No. 1,101,101). Resistor 20 is included between the sensing electrode and the operational amplifier in order to slow the response time of the sensor and thus provide immunity from electronic noise and fluctuations in the potential of the sensing electrode; the value of resistor 20 is generally chosen between 0 and 500 ohms.

The amplifier 18 has an offset null potentiometer 19 which is usually set such that current is supplied by the amplifier to its output unless there is no potential difference between the two inputs of the amplifier; however, the offset null can be set to provide an offset voltage between the amplifier inputs, in which case current is supplied by the amplifier to its output unless the potential between the amplifier inputs is a certain, non-zero value (the offset voltage). When an offset voltage is set, the amplifier will supply current to its output and to the sensor until a potential difference is created between its inputs that equals the offset voltage and when this occurs, there is a potential difference between the sensing electrode and the electrolyte immediately surrounding it; the presence of a layer of electrolyte around an electrode that is at a different potential to the electrode is termed a 'double layer' and acts like a capacitor.

It is usual to adjust the potentiometer 19 to trim the offset null of the amplifier 18 to substantially zero so that, when the monitor is switched on, there is no voltage difference between the reference electrode and the sensing electrode and so there is no charging of the double layer on the sensing electrode which would give a spurious reading when the monitor is first switched on. In some monitors a substantial voltage offset is maintained between the sensing and reference electrodes in order to minimise cross-sensitivity with gases other than the gas that it is desired to detect which may be present in the atmosphere being monitored and such an arrangement is used in particular to minimise cross-sensitivity to hydrogen gas; however when a large offset is established between the sensing and the reference electrode, it can take 2 days for a sensor to settle to a steady state when the monitor is first switched on (and no accurate readings can be taken during this period) and such monitors are normally kept permanently switched on to avoid this problem.

If the sensor, which is a replaceable item, is not correctly installed in the monitor, e.g. if the electrode terminals of the sensor do not properly contact the corresponding terminals of the monitor, the monitor will show a zero reading, even if there is gas in the atmosphere being detected and the user will assume that the atmosphere contains no gas of the type being monitored. Since monitors can detect poisonous gases, e.g. carbon monoxide, this can be dangerous. Thus, the circuit of the above type is not 'fail-safe'. A further problem can arise if the electrolyte of the sensor cell 10 evaporates so that the cell dries out and no longer conducts electric current; in this case, a zero reading is again obtained even if there is gas in the atmosphere being monitored.

It has been proposed in CH-636 447 to check that a pH reference (or counter) electrode is operating properly in a potentiometric titration apparatus by measuring the resistance between the counter and the sensing electrodes of the titration apparatus by passing an alternating current between these electrodes, rectifying the resulting current, passing an identical alternating current through a fixed resistor, rectifying the resulting current and subtracting the two rectified currents from each other to form a signal and stopping the titration if the said signal indicates that the resistance between the sensing electrode and the counter electrode is either much higher or much lower than the resistance of the fixed resistor. Apart from being applied in a different technical field to the present invention (CH-636 447 uses potential as a sensing criterion rather current as is the case with the present invention), the proposal in CH-636 447 is complex and hence expensive to implement.

EP 0 039 549 describes a system for testing the operation of electrochemical gas sensors having a salt solution electrolyte by applying a pulse of potential between the electrodes of the sensor that decomposes the electrolyte; if there is a resulting change in current flowing through the sensor, then the sensor is operating properly. The electrolysis of the electrolyte causes gas to be generated, which is disadvantageous in a sealed gas sensor since it can affect the sensor operation and pressure can build up within the sensor causing it to leak; the present provides a system that avoids these problems.

DISCLOSURE OF THE INVENTION

The present invention is based on the concept that the potential across the double layer at the sensing electrode of a three electrode sensor cannot be changed instantaneously because of the large capacitance of the double layer and the resistance of the rest of the circuit. If the potential between the reference electrode and the sensing electrode is changed, a current will flow until the double layer capacitance is charged to a new potential and this flow of current can be detected and used to confirm that the sensor is working properly; if, however, the sensor is not working properly (or is absent), a reduced current (or no current) will flow as a result of the potential being imposed and this reduced (or non-existent) current can be used to provide a warning that the sensor is not working properly. One advantage of the present invention is that, providing the imposed potential is applied only for a short time, the double layer reverts to its operational potential when the imposed potential is removed within a very short time (a fraction of a millisecond) and normal operation of the sensor can then be continued and so the time that the sensor is not operating to monitor the atmosphere is minimal. It is not necessary for the double layer to be completely charged in the operation of the present invention and indeed the partial charging of the double layer is preferred.

According to the present invention, there is provided a gas monitor for detecting the presence of a certain gas in an atmosphere being monitored, which monitor comprises:

an amperometric electrochemical gas sensor comprising electrolyte and a sensing electrode, a reference electrode and a counter electrode, all in contact with the electrolyte;

means capable in operation of maintaining a first potential (or average potential) between the sensing- and reference-electrodes when there is no gas in the atmosphere of the type being monitored, means for impressing a pulsed second potential between the reference electrode and the sensing electrode, which second potential is different from the first potential (or average potential) and is insufficient to cause a potential within the sensor that electrolyses the sensor electrolyte, means for detecting a current flowing at the sensing electrode or at the counter electrode when the said second potential is impressed, and means for giving an indication that the sensor is not working properly when the said current is less than a threshold value.

The means for maintaining the first potential (or average potential) is preferably an operational amplifier having inputs connected directly or indirectly to the sensing- and reference-electrodes and an output connected either to the counter electrode or to the sensing electrode. The first potential (or average potential) is preferably zero.

The pulses of second potential between the reference electrode and the sensing electrode may be impressed in several ways, for example:

(a) the balance of the operational amplifier may be disturbed so that the amplifier produces an output for a short time, e.g. the offset null of the operational amplifier may be disturbed so that the amplifier produces an offset voltage (or a different offset voltage), or (b) a voltage may be impressed between the two electrodes from a voltage source, which usually will be the power source of the monitor; the voltage may be a short-lived pulse or a fluctuating voltage, e.g. an alternating voltage, that is continuously or periodically impressed between the two electrodes. If the voltage source provides a fluctuating voltage, the period of the fluctuations should preferably be shorter than the response time of the monitor output (i.e. the device measuring the current flowing through the sensor cell and giving an indication of the amount of the gas being monitored in the atmosphere) so that the output signal of the monitor in the presence of the gas to be detected will not be influenced by the imposed voltage; likewise the period of the fluctuations is preferably longer than the response time of the device for detecting the current resulting from the imposition of the second voltage. Furthermore, it is preferred that the fluctuating voltage should average out to zero so that the reading produced by the sensor in the presence of the gas to be detected is not affected by the imposed fluctuating voltage. As will be appreciated, when the imposed voltage is an alternating (or other wave-form) voltage, the said first potential between the sensing- and the reference-electrodes will be the average voltage of the imposed voltage whereas the second voltage will be the peak (or trough) of the alternating voltage.

According to a second aspect of the present invention, there is provided a method of testing the operation of an amperometric electrochemical sensor in a gas monitor, the sensor comprising an electrolyte and a sensing-, a reference- and a counter-electrode all of which are in contact with the electrolyte, which method comprises:

maintaining a first potential (or average potential) between the sensing- and reference-electrodes when there is no gas in the atmosphere of the type being monitored, impressing a second potential between the reference electrode and the sensing electrode, which second potential is different from the first potential (or average potential) and is insufficient to cause a potential within the sensor that electrolyses the sensor electrolyte, detecting the current flowing at the sensing electrode or at the counter electrode when the said second potential is impressed;

comparing the said current with a threshold value, and giving an indication that the sensor is faulty if the current falls below the said threshold.

When the sensor is in a steady state (usually occurring when there is no gas of the type being detected in the atmosphere being monitored), the imposition of the second potential between the reference electrode and the sensing electrode causes a current to flow in the sensor which charges the double layer at the sensing electrode. While the double layer is being charged, a substantial current can flow through the sensor and the external circuit and this current decays as the double layer is charged. The rate at which the double layer is charged depends on the resistance in the external circuit in the monitor and in particular on the resistance between the sensing electrode and its corresponding input into the operational amplifier. The current that flows while the double layer is being charged can be detected relatively easily by a device within the monitor. Hitherto, there has been no proposal to use such an offset current to provide confirmation that the sensor is working.

In contrast to the device proposed in CH-636 447, the sensor monitoring system of the present invention measures the capacitance of the double layer at the sensing electrode, whereas the device of CH-636 447 measures the resistance of the electrolyte between the sensing and reference electrodes.

BRIEF DESCRIPTION OF THE DRAWINGS

The present invention will now be described in greater detail, by way of example only, with reference to the accompanying drawings in which.

BEST MODES FOR CARRYING OUT THE INVENTION

In FIGS. 1 to 7, the same reference numbers will be used to indicate comparable components.

Figure 1:
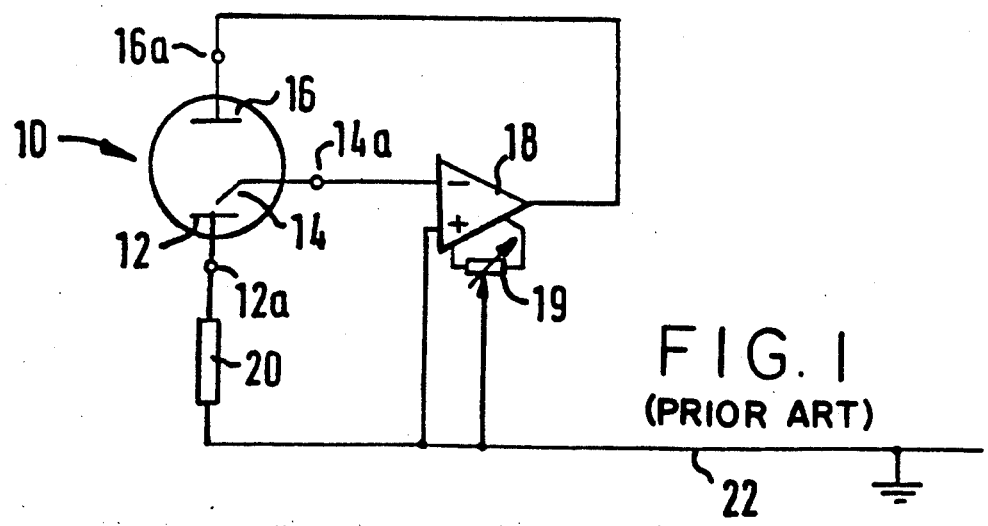
FIG. 1 is a known circuit for a gas monitor.
Figure 2:
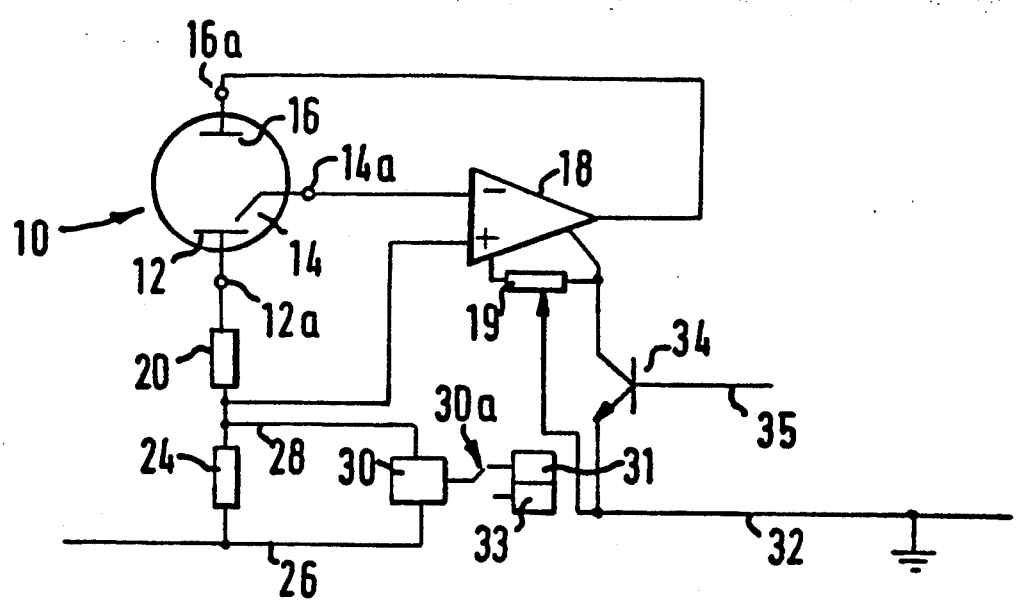
FIGS. 2 to 7 are gas monitor circuits of the present invention.

The circuit shown in FIG. 2 is identical to that of FIG. 1 with two exceptions: the first difference lies in that the current flowing through the sensor is detected across a high value resistor 24 connected between a fixed voltage line 26 and a further line 28 by means of a high impedance potentiometer 30. The working of this type of circuit is described in greater detail in European Patent Specification 0,220,896A; the current flowing through resistor 24 is the same as that flowing through the sensor cell because the impedance between the inputs of the amplifier 18 is large and because the potentiometer 30 is of high impedance; by making the value of resistor 24 large (e.g. 10 kohms) the voltage drop across resistor 24 is large and this can be used directly (i.e. without further amplification) to drive an output device 31, which can be, for example, a voltmeter or a display.

The second difference lies in the connection of the offset null 19 to an earth line 32 via a transistor 34. Usually, the transistor is non-conductive but a pulse may be supplied along control line 35 which renders the transistor conducting and so connects the potentiometer 19 to the earth line, thereby upsetting the offset null and driving the amplifier 18 to provide an output current causing a current to flow through the sensor and through the resistors 20 and 24 which will charge the double layer and generate a potential difference between the sensing electrode and the reference electrode. The current can be detected by an alarm device 33 connected to the potentiometer 30 by a switch 30a while the sensor is being tested; the switch 30a is operated by means (not shown) to connect the potentiometer to alarm 33 for the time that the monitor is under test, i.e. while the pulse is supplied along control line 35 to the transistor 34, but otherwise the switch 30a is arranged to connect the potentiometer to the output device 31. If the signal from the potentiometer 30 to the alarm device 33 is less than a threshold value then the device 33 emits a visible and/or audible alarm indicating that the sensor is not working properly.

Instead of transistor 34, any switching device can be used to connect the offset potentiometer 19 to the earth line 32, e.g. a field effect transistor, an integrated circuit, a relay etc.

If the sensor is not correctly connected to the terminals 12a, 14a or 16a or if the electrolyte in the sensor cell has evaporated to such an extent that the sensor no longer works properly, then no current (or a reduced current) will flow as a result of the upsetting of the null offset and the alarm device 33 will then be triggered; it will be appreciated that the correct connection of all three terminals of the sensor is required for a current to flow through the sensor.

The pulse to the control 35 of transistor 34 can be sent when the monitor is first switched on or periodically during its operation. The duration of the pulse should be sufficient to allow the alarm 33 to register the current resulting from the upsetting of the offset null but is should be kept to a minimum to minimise the period in which the monitor is being tested (and hence not monitoring the atmosphere); we have found that a pulse duration of 1 to 10 milliseconds has proved satisfactory. Because the current flowing through the sensor and the external monitor circuit is indistinguishable from the current resulting from the presence of a gas in the atmosphere being sensed, it is desirable that the pulse to transistor 34 is supplied while the monitor is put into a test mode during which the normal output device 31 of the monitor (e.g. a display, a voltmeter or an alarm) is disconnected since otherwise the output device might give a spurious reading. During the test mode, the potentiometer 30 is, as mentioned above, connected via a switch 30a to the alarm 33.

If there is a current flowing through the sensor as a result of the presence of the depolarising gas in the atmosphere being monitored, this does not affect the test routine since the detection of a current (whether due to a depolarising gas or the upsetting of the offset null) is indicative that the sensor is working properly.

Once the test routine is completed, the normal operation of the monitor is resumed by re-connecting the normal output device 31 to the potentiometer 30 by means of a switch 30a. A typical test routine might last approximately 1 millisecond and so the down-time for the monitor is negligible.

Figure 3:
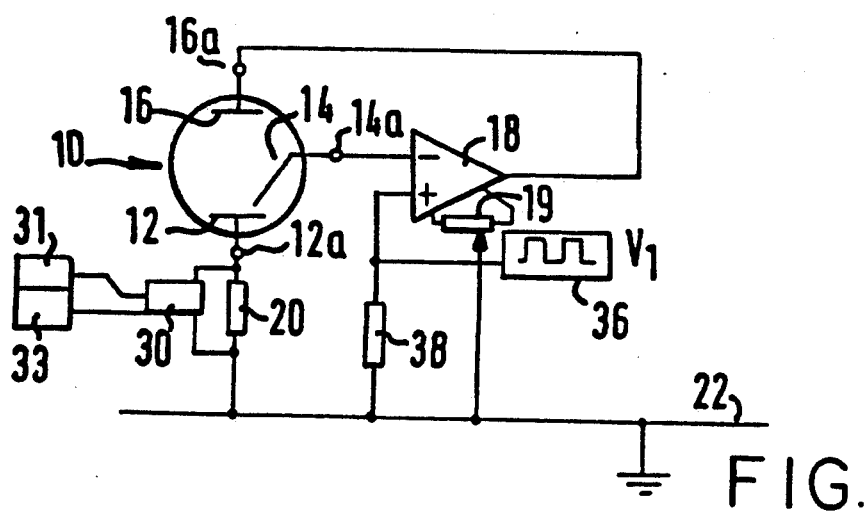
Figure 4:
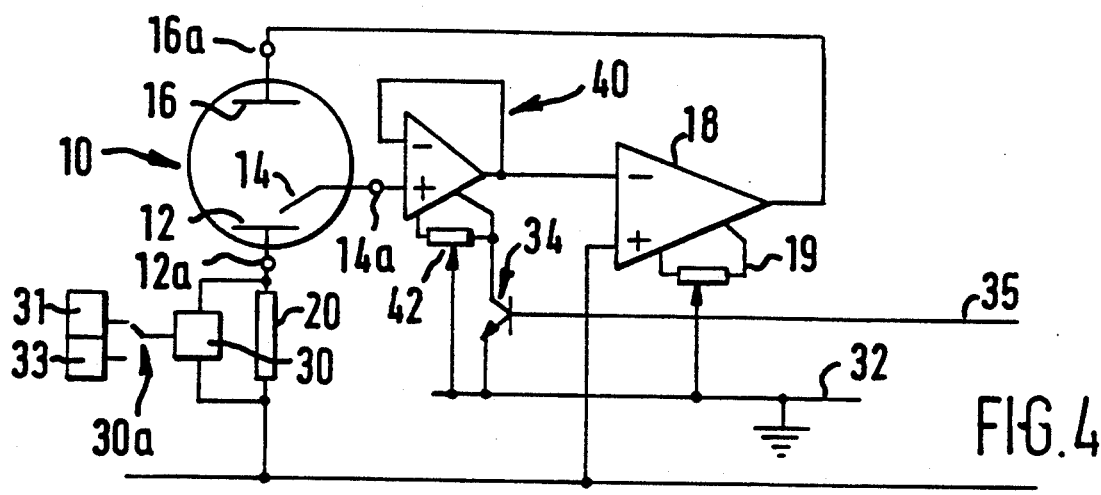

It is not necessary for the monitor to be switched into a test mode to put the present invention into operation; the circuit shown in FIG. 3 includes a square wave generator 36 (although any other shape of wave or pulse may be used) which superimposes an oscillating potential between the sensing electrode 12 and the reference electrode 14 causing an oscillating current to flow through the sensor cell 10 which can be detected by potentiometer 30. If the average current caused to flow as a result of the oscillating potential is zero then the net output recorded by output device 31 will be unaffected by the superimposed voltage. Temporary fluctuations in the signal fed from the potentiometer 30 to the output device 31 could be eliminated by making the duration of each cycle of the oscillating potential shorter than the response time of the output device 31 or by placing a suitable filter or buffer between the switch 30a and the output device 31 to slow the response time of the latter. An additional resistor 38 is included between the potential source 36 and the sensing electrode 12 across which the oscillating voltage is impressed. The alarm 33 is triggered if the potentiometer indicates no current flowing for a period of time corresponding to at least one cycle of the alternating current. It will be evident that the response time of the alarm 33 should be sufficiently fast to register the fluctuations in the potential across the resistor 20 caused by the oscillating potential of the wave generator 36.

Instead of upsetting the balance of amplifier 18 via its offset null (as in FIG. 2) in order to provide a potential between the reference and the sensing electrode, the balance of the amplifier 18 can instead be upset by adding a signal to one of the amplifier inputs. This is achieved in the circuit shown in FIG. 4 by including a buffer amplifier 40 between the reference electrode 14 and the operational amplifier 18 and connecting the offset null 42 of the buffer amplifier to the earth line 32 via transistor 34. When a pulse is sent along the control 35 of the transistor 34, thereby rendering it conductive, the offset null of buffer amplifier 40 is upset, thereby causing a current to be supplied by the output of buffer amplifier 40 to one of the inputs of amplifier 18 and so causing the output of amplifier 18 to provide a current to the counter electrode 16, which results in a current through the cell if it is functioning correctly and this can be detected by the alarm device 33; if the signal to the alarm device 33 from potentiometer 30 is below a threshold value, it generates an alarm.

Figure 5:
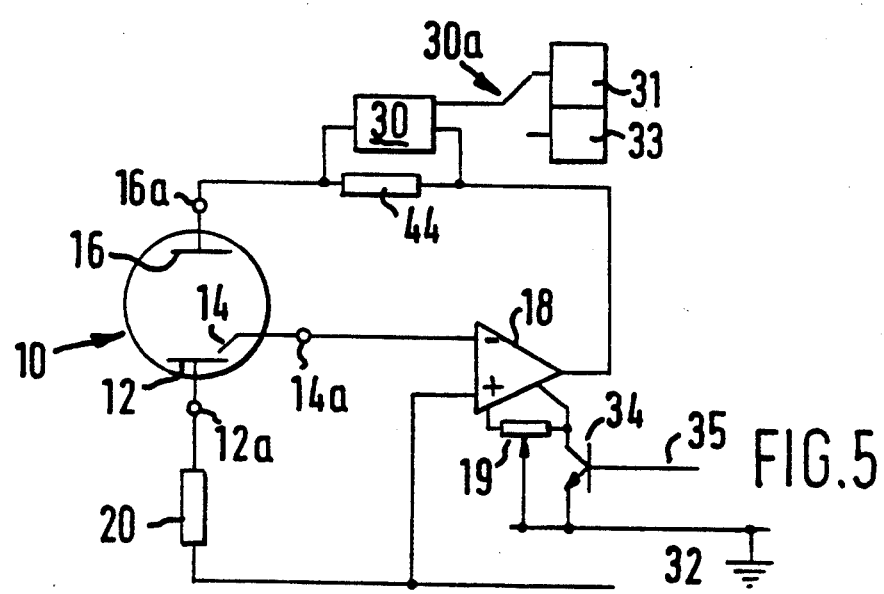

In FIG. 5, the current flowing through the cell is detected as a voltage drop across resistor 44 connected between the output of amplifier 18 and the counter electrode 16.

Figure 6:
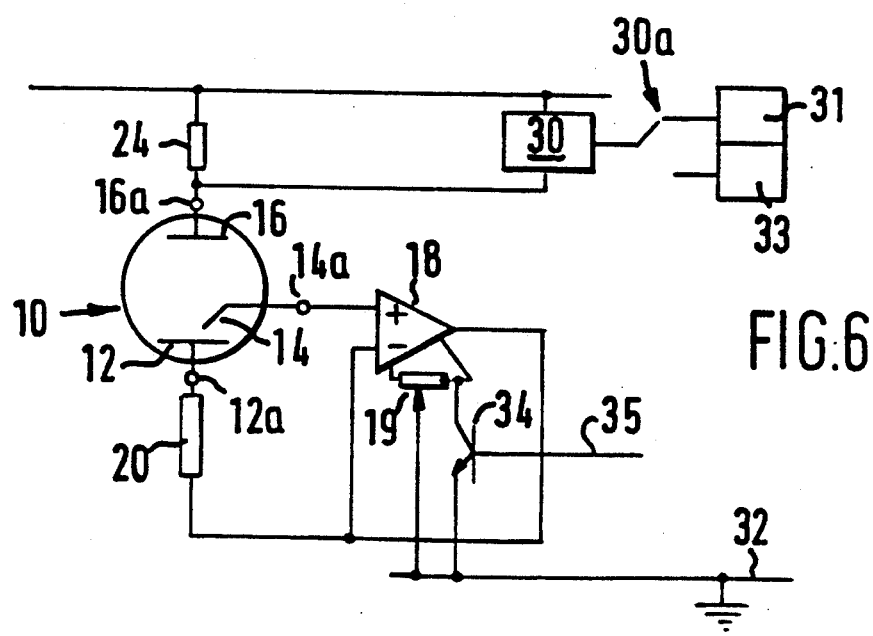

FIG. 6 is identical to FIG. 2 except that the output of the amplifier 18 is connected to the sensing electrode 12 and the resistor 24 is connected to the counter-electrode.

Figure 7:
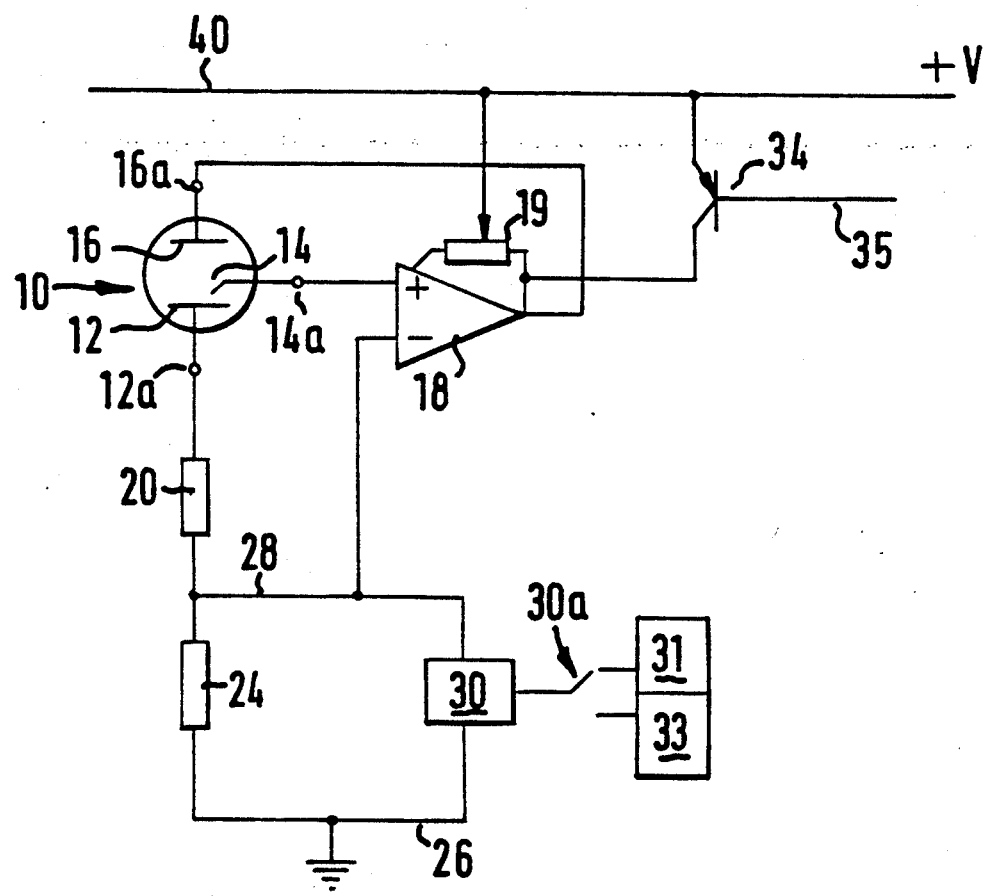

FIG. 7 is identical to FIG. 2 except that the offset null potentiometer 19 is connected to the positive voltage rail 40 of the monitor instead of the earth rail 32.

The initiation of the test routine can be controlled by a microprocessor unit within the monitor, in which case the sensor current could be continually monitored by periodically initiating a test routine and also the switch 30a would not then be required as the microprocessor could control the output and alarm devices 31 and 33.

I claim:

1. A gas monitor for detecting the presence of a certain gas in an atmosphere being monitored, which monitor comprises:
   an amperometric electrochemical gas sensor comprising electrolyte and a sensing electrode, a reference electrode and a counter electrode all in contact with the electrolyte,
   means for maintaining an average value for a first potential between the sensing- and reference-electrodes when there is no gas in the atmosphere of the type being monitored,
   means for impressing at least one pulse of potential or for impressing a fluctuating potential between the reference electrode and the sensing electrode, the peak potential of each pulse or of the said fluctuating potential being a second potential that is different from the first potential (or average potential) and that is insufficient to cause a potential within the sensor that electrolyses the sensor electrolyte,
   means for detecting a current flowing at the sensing electrode or at counter electrode when the said second potential is impressed, and
   means for giving an indication when the said current is less than a threshold value.

2. A monitor as claimed in claim 1, wherein the first potential is zero.

3. A monitor as claimed in claim 1, wherein the means for maintaining the first potential is an operational amplifier having inputs connected directly or indirectly to the sensing- and reference-electrode and an output connected either to the counter electrode or to the sensing electrode.

4. A monitor as claimed in claim 3, wherein the second potential between the reference electrode and the sensing electrode is impressed by disturbing the balance of the amplifier.

5. A monitor as claimed in claim 4, wherein the amplifier has an offset null and the balance of the amplifier is disturbed by disturbing the offset null so that the amplifier produces an offset voltage.

6. A monitor as claimed in claim 4, wherein the balance of the amplifier is disturbed by adding a signal to an input of the amplifier.

7. A monitor as claimed in claim 1, wherein the second potential between the reference electrode and the sensing electrode is impressed by an independent voltage source, preferably derived from the power supply of the monitor.

8. A monitor as claimed in claim 7, wherein the second potential is impressed as a fluctuating voltage that is continuously or periodically impressed between the sensing- and the reference-electrodes or as a short-lived pulse.

9. A monitor as claimed in claim 8, wherein the independent voltage source provides a fluctuating voltage, wherein the monitor further includes output means for measuring the current flowing through the gas sensor and providing an output signal giving an indication of the amount of the gas being monitored in the atmosphere and wherein the period of the voltage fluctuations provided by the said independent voltage source is shorter than the response time of the monitor output so that the signal from the output means in the presence of the gas to be detected will not be influenced by the imposed fluctuating voltage.

10. A monitor as claimed in claim 9, wherein the the fluctuating voltage is such that it averages zero so that the average current flowing through the sensor in the absence of the gas to be detected is substantially zero.

11. A method of testing the operation of an amperometric electrochemical sensor in a gas monitor, the sensor comprising electrolyte and a sensing-, a reference- and a counter-electrode in contact with the electrolyte, which method comprises:

maintaining a first potential at an average value between the sensing- and reference-electrodes when there is no gas in the atmosphere of the type being monitored, impressing at least one pulse of potential or a fluctuating potential between the reference electrode and the sensing electrode, the peak potential of each pulse or of the said fluctuating potential being a second potential that is different from the first potential and that is insufficient to cause a potential within the sensor that electrolyses the sensor electrolyte, detecting the current flowing at the sensing electrode or at the counter electrode when the said second potential is impressed, comparing the said current with a threshold value, and giving an indication that the sensor is faulty if the current falls below the said threshold.

* * * * *